United States Patent
Tsunashima

(10) Patent No.: US 10,745,706 B2
(45) Date of Patent: Aug. 18, 2020

(54) **METHOD FOR GENE TRANSFER INTO SORGHUM PLANT USING *AGROBACTERIUM*, AND METHOD FOR PRODUCTION OF TRANSGENIC SORGHUM PLANT**

(71) Applicant: JAPAN TOBACCO INC., Tokyo (JP)

(72) Inventor: Masako Tsunashima, Shizuoka (JP)

(73) Assignee: JAPAN TOBACCO INC., Tokyo (JP)

(*) Notice: Subject to any disclaimer, the term of this patent is extended or adjusted under 35 U.S.C. 154(b) by 67 days.

(21) Appl. No.: 15/539,523

(22) PCT Filed: Dec. 24, 2015

(86) PCT No.: PCT/JP2015/085979
§ 371 (c)(1),
(2) Date: Jun. 23, 2017

(87) PCT Pub. No.: WO2016/104583
PCT Pub. Date: Jun. 30, 2016

(65) Prior Publication Data
US 2018/0010139 A1    Jan. 11, 2018

(30) Foreign Application Priority Data

Dec. 24, 2014 (JP) ................... 2014-259772

(51) Int. Cl.
  *C12N 15/82* (2006.01)
  *A01H 4/00* (2006.01)
  *A01H 6/46* (2018.01)
(52) U.S. Cl.
  CPC ......... *C12N 15/8205* (2013.01); *A01H 4/005* (2013.01); *A01H 6/4666* (2018.05)
(58) Field of Classification Search
  None
  See application file for complete search history.

(56) References Cited

U.S. PATENT DOCUMENTS

| | | | |
|---|---|---|---|
| 6,369,298 B1 * | 4/2002 | Cai .................... | C12N 15/8205 435/419 |
| 6,455,761 B1 * | 9/2002 | Kuvshinov ........ | C12N 15/8205 435/430.1 |
| 2006/0143728 A1 * | 6/2006 | Shi ...................... | C07K 14/415 800/278 |
| 2007/0163007 A1 | 7/2007 | Ishida | |
| 2010/0132066 A1 | 5/2010 | Ishida et al. | |
| 2010/0132068 A1 | 5/2010 | Takakura et al. | |
| 2011/0167516 A1 * | 7/2011 | Gordon-Kamm ........................ | C12N 15/8213 800/278 |
| 2012/0124696 A1 | 5/2012 | Ishida et al. | |

FOREIGN PATENT DOCUMENTS

| | | | | |
|---|---|---|---|---|
| JP | 2006-141252 | * | 6/2006 | ............... A01H 4/00 |
| WO | WO 2005/017152 A1 | | 2/2005 | |
| WO | WO 2007/148819 A1 | | 12/2007 | |
| WO | WO 2008/105509 A1 | | 9/2008 | |
| WO | WO 2011/013764 A1 | | 2/2011 | |

OTHER PUBLICATIONS

Casas et al. PNAS USA 90: 11212-11216 (1993).*
Olhoft et al. Planta 216: 723-735 (2003).*
Toyoma et al. Molecules and Cells 16(1): 19-27 (2003).*
Julkifle et al. Australian Journal of Basic and Applied Sciences 4(8): 3424-3432 (2010).*
Subramaniam et al. World Applied Sciences Journal 7(10): 1295-1307 (2009).*
Eapen et al. Plant Cell Tissue and Organ Culture 51(3): 229-232 (1997).*
Cameron et al. Scientia Horticulturae 19: 373-378 (1983).*
Schenk et al. Canadian Journal of Botany 50(1): 199-204 (1972).*
Vakili et al. Physiologu and Molecular Biology of Plants 24(4): 703-710 (Aug. 2018).*
Wier et al. Australian Journal of Plant Pathology 28: 807-818 (2001).*
Hiei et al. Frontiers in Plant Science 5: Article 628, 11 pages (Nov. 2014).*
Mysore et al. PNAS 97(2): 948-953 (Jan. 2000).*
Shen, H. PhD Thesis, University of Leiden, 26 pages (Jan. 2017).*
Kovalchuk et al. The EMBO Journal 19(17): 4431-4438 (2000).*
Bent et al. Plant Molecular Biology, Manual B7, pp. 1-14 (1998).*
Office Action dated Aug. 14, 2018, in Chinese Patent Application No. 201580070896.3.
Ye et al., "A Review of Some Assisted Strategies for Improving the Efficiency of *Agrobacteruim*-Mediated Plant Transformation," Chinese Agricultural Science (2012), vol. 45, No. 15, pp. 3007-3019, with English abstract and partial English translation.
Boyko et al., "High frequency Agrobacterium tumefaciens-mediated plant transformation induced by ammonium nitrate," Plant Cell Reports, vol. 28, 2009 (Published Online: Feb. 17, 2009), pp. 737-757.

(Continued)

*Primary Examiner* — David T Fox
(74) *Attorney, Agent, or Firm* — Birch, Stewart, Kolasch & Birch, LLP

(57) ABSTRACT

The problem to be solved by this invention is to provide a method of gene introduction for a genus Sorghum plant and a method for producing a transformed genus Sorghum plant with a higher efficiency than the conventionally known *Agrobacterium* method. This invention provides a gene introduction method of a genus Sorghum plant characterized by using a medium with an increased concentration of a nitrogen source and/or an increased concentration of inorganic ions selected from magnesium ion, potassium ion, calcium ion and sodium ion, in a step of preparing a plant tissue material of a genus Sorghum plant, a step of inoculation with *Agrobacterium* and/or a co-cultivation step. This invention also provides a method for producing a transformed plant using the gene introduction method of this invention.

10 Claims, No Drawings

Specification includes a Sequence Listing.

(56) References Cited

OTHER PUBLICATIONS

Boyko et al., "Potassium chloride and rare earth elements improve plant growth and increase the frequency of the Agrobacterium tumefaciens-mediated plant transformation," Plant Cell Reports, vol. 30, No. 4, 2011 (Published Online: Dec. 5, 2010), pp. 505-518.
Cai et al., "Callus induction and plant regeneration from shoot portions of mature embryos of high tannin sorghums," Plant Cell, Tissue and Organ Culture, vol. 9, No. 3, Sep. 1987, pp. 245-252.
Cheng et al., "Genetic transformation of wheat mediated by Agrobacterium tumefaciens," Plant Physiol., vol. 115, No. 3, Nov. 1997, pp. 971-980.
Du et al., "Effects of basal media, salt concentrations, antioxidant supplements and co-effects on the Agrobacterium-mediated transformation efficiency in maize," African Journal of Biotechnology, vol. 9, No. 8, Feb. 22, 2010, pp. 1135-1143.
Elkonin et al., "Influence of nitrogen and phosphorus on induction embryogenic callus of sorghum," Plant Cell, Tissue and Organ Culture, vol. 61, No. 2, May 2000, pp. 115-123.
Elkonin et al., "Initiation and maintenance of friable, embryogenic callus of sorghum (*Sorghum bicolor* (L.) Moench) by amino acids," Maydica, vol. 40, No. 2, 1995, pp. 153-157.
Gao et al., "Efficient genetic transformation of Sorghum using a visual screening marker," Genome, vol. 48, No. 2, 2005 (published online Feb. 28, 2005), pp. 321-333.
Gurel et al., "Efficient, reproducible Agrobacterium-mediated transformation of sorghum using heat treatment of immature embryos," Plant Cell Rep, vol. 28, No. 3, 2009 (published online Dec. 30, 2008), pp. 429-444 (16 pages total).
Hiei et al., "Efficient transformation of rice (*Oryza sativa* L.) mediated by Agrobacterium and sequence analysis of the boundaries of the T-DNA," The Plant Journal, vol. 6, No. 2, Aug. 1994, pp. 271-282 (13 pages total).
Hiei et al., "Improved frequency of transformation in rice and maize by treatment of immature embryos with centrifugation and heat prior to infection with Agrobacterium tumefaciens," Plant Cell Tiss Organ Cult, vol. 87, No. 3, 2006 (published online: Oct. 12, 2006), pp. 233-243.
International Search Report (Form PCT/ISA/210), dated Mar. 22, 2016, for International Application No. PCT/JP2015/085979.
Ishida et al., "High efficiency transformation of maize (*Zea mays* L.) mediated by Agrobacterium tumefaciens," Nature Biotechnology, vol. 14, No. 6, Jun. 1996, pp. 745-750.
Liu et al., "Additive effects of three auxins and copper on sorghum in vitro root induction," In Vitro Cell.Dev.Biol.-Plant, vol. 49, No. 2, 2013 (published online Jan. 15, 2013), pp. 191-197.
Tingay et al., "Agrobacterium tumefaciens-mediated barley transformation," Plant J., vol. 11, No. 6, Jun. 1997, pp. 1369-1376.
Vega et al., "Improvement of Agrobacterium-mediated transformation in Hi-II maize (*Zea mays*) using standard binary vectors," Plant Cell Reports, vol. 27, No. 2, 2008 (published online Oct. 16, 2007), pp. 297-305.
Wu et al., "Optimized Agrobacterium-mediated sorghum transformation protocol and molecular data of transgenic sorghum plants," In Vitro Cell.Dev.Biol.-Plant, vol. 50, No. 1, 2014 (published online Dec. 13, 2013), pp. 9-18.
Zhao et al., "Agrobacterium-mediated sorghum transformation," Plant Molecular Biology, vol. 44, No. 6, Dec. 2000, pp. 789-798.

\* cited by examiner

SEQUENCE LISTING

<160> NUMBER OF SEQ ID NOS: 2

<210> SEQ ID NO 1
<211> LENGTH: 30
<212> TYPE: DNA
<213> ORGANISM: Artificial sequence
<220> FEATURE:
<223> OTHER INFORMATION: Forward primer

<400> SEQUENCE: 1
atggacccag aacgacgccc ggccgacatc         30

```
<210> SEQ ID NO 2
<211> LENGTH: 30
<212> TYPE: DNA
<213> ORGANISM: Artificial sequence
<220> FEATURE:
<223> OTHER INFORMATION: Reverse primer

<400> SEQUENCE: 2
tcagatctcg gtgacgggca ggaccggacg                                    30
```

METHOD FOR GENE TRANSFER INTO SORGHUM PLANT USING AGROBACTERIUM, AND METHOD FOR PRODUCTION OF TRANSGENIC SORGHUM PLANT

TECHNICAL FIELD

The present invention relates to a method of gene introduction into a genus *Sorghum* plant via *Agrobacterium*. The present invention also relates to a method of producing a transformed genus *Sorghum* plant via *Agrobacterium*.

BACKGROUND ART

*Sorghum* is a short-day monocotyledon of the Poaceae family originating in Africa. *Sorghum* has a high water use efficiency, as well as excellent drought resistance and high-temperature resistance, and it is a major cereal crop next to corn, rice, wheat and barley, constituting an important food supply in African and Asian countries. Because *Sorghum* has a high sugar content and can be a raw material for bioethanol, much effort is put into technological developments to modify the agricultural characteristics of *Sorghum*. The genome sequencing of *Sorghum* has been completed, and an analysis of genes involved in the useful agricultural characteristics specific to *Sorghum* as well as of the quantitative trait locus (QTL) is in progress. The technological development of *Sorghum* gene recombination is considered a crucial factor in modifying the agricultural characteristics of *Sorghum*.

Physicochemical methods (direct introduction of DNA), such as a polyethylene glycol method, an electroporation method, and a particle gun method, and biological methods (indirect introduction of DNA) utilizing functions of *Agrobacterium* are known as methods for transformation of monocotyledons such as barley, wheat, corn, and rice, which are major cereal crops. In the gene introduction mediated by *Agrobacterium* (hereinafter referred to as the *Agrobacterium* method), the regulation of expression of gene groups in a Ti plasmid virulence region (vir region) maintains a small number of copies of an objective gene and prevents a gene from being introduced as fragmented segments. The gene introduction mediated by *Agrobacterium* therefore has notable advantages of providing a large number of transformants highly expressing the objective gene and of allowing the difference in expression levels among individual transformants to be small compared to the direct gene introduction.

The *Agrobacterium* method is universally used for transformation of dicotyledons. Although it has been believed for a long time that hosts of *Agrobacterium* in nature are limited only to dicotyledons and that *Agrobacterium* has no ability to infect monocotyledons, a method of a highly efficient transformation of a monocotyledon by *Agrobacterium* has been reported, the first of which was in a major cereal crop, rice, as a result of detailed studies such as investigation of tissue materials, improvements in medium compositions, and selection of *Agrobacterium* strains (Hiei et al., 1994: Non-Patent Document 1). Then, following on the success in rice, examples of successful transformation mediated by *Agrobacterium* in corn (Ishida et al., 1996: Non-Patent Document 2), wheat (Cheng et al., 1997: Non-Patent Document 3), barley (Tingay et al., 1997: Non-Patent Document 4), and *Sorghum* (Zhao et al., 2000: Non-Patent Document 5) have been reported.

1. Known Technologies for Transformation of *Sorghum* by the *Agrobacterium* Method 1) Plant Tissue Inoculated with *Agrobacterium*

An immature embryo is used as the tissue of *Sorghum* to be inoculated with *Agrobacterium* (Non-Patent Document 5).

2) Pre-Treatment

A thermal treatment or a centrifugation treatment of the plant material to be transformed is used in several examples of transformation to a monocotyledon plant as a method to improve the transformation efficiency of the *Agrobacterium* method (Hiei et al. 2006: Non-Patent Document 6). It has been reported that the transformation efficiency of *Sorghum* also increased when immature embryos were treated at 43° C. for 3 min before infection by *Agrobacterium*, so that the transformation efficiency of the treated plot increased by about three folds relative to a non-treated plot (Gurel et al. 2009: Non-Patent Document 7). With regard to the centrifugation treatment, however, it is written that the treatment had a negative effect on the transformation of *Sorghum*.

3) Co-Cultivation Step

This step is a step of inoculating a plant tissue with *Agrobacterium* to co-cultivate the plant tissue and *Agrobacterium*. MS medium which contains a one-time amount of MS Inorganic Salts as the composition of a co-cultivation medium is used in the transformation of *Sorghum* mediated by *Agrobacterium* (Non-Patent Document 5).

4) Callus Formation Step

The callus formation step is a step for dedifferentiating plant tissues.

Callus formation tends to be inhibited in the *Sorghum* tissue culturing step due to excessive generation of phenol compounds (Cai et al. 1987: Non-Patent Document 8). Meanwhile, it has been reported that an addition of L-proline and L-asparagine to the MS medium accelerated the growth of embryogenic callus and suppressed the generation of phenol compounds which constitutes an inhibitory cause against culturing *Sorghum* (Elkonin et al. 1995: Non-Patent Document 9). It has also been reported that an increased nitrate ion concentration and phosphate ion concentration promoted the induction of embryogenic callus and improved the regeneration efficiency from callus to a plant (Elkonin et al. 2000: Non-Patent Document 10). It is also reported that an addition of polyvinylpolypyrrolidone (PVPP) to a callus formation medium reduces the browning of cells from damages that occurred when the cell was inoculated with *Agrobacterium* (Gao et al. 2005: Non-Patent Document 11).

As an exemplary case of an actual *Sorghum* transformation, there is a report that the transformation efficiency improved by using 6-benzylaminoproline (BAP) as the plant growth regulator to be added to the callus formation medium (resting medium and selection medium) (Wu et al. 2014: Non-Patent Document 12).

5) Regeneration Step

There are attempts to optimize the types and concentrations of plant growth regulators to be added to the regeneration medium. It has been reported that regeneration of roots from the regenerated plant transplanted to a rooting medium is promoted by using MS medium that includes 1 mg/L naphthaleneacetic acid (NAA), 1 mg/L indole-3-acetic acid (IAA), 1 mg/L indole-3-butyric acid (IBA) and 1 μmol/L copper sulfate (Guoquan et al. 2013: Non-Patent Document 13).

The transformation method of *Sorghum* mediated by *Agrobacterium* has been modified as shown above, and the transformation efficiency that was 2.1% (Non-Patent Document 5) in the first report increased to 33% (Non-Patent Document 12). However, this transformation efficiency is still not high enough relative to rice or corn.

2. Modification of Co-Cultivation Medium in Plant Transformation Mediated by *Agrobacterium* Bacteria Multiple reports have been provided in relation to corn regarding transformation mediated by *Agrobacterium* of an improvement in transformation efficiency by the use of a co-cultivation medium consisting of a diluted N6 medium. For example, Du et al. showed that among corn (A188) immature embryos inoculated with *Agrobacterium*, the rate of immature embryos exhibiting transient expression of GUS genes increased to 90% or higher for all N6 mediums whose main inorganic salts were diluted to 50%, 30% or 10% relative to 72% in N6 medium containing N6 Inorganic Salts at a one-time amount (Du et al. 2010: Non-Patent Document 14).

Furthermore, another report on corn (Hi-II) demonstrates that while a use of an *Agrobacterium* suspension medium and a co-cultivation medium each containing N6 Inorganic Salts at a one-time amount resulted in 0% transformation efficiency per contesting callus, a use of an *Agrobacterium* suspension medium and a co-cultivation medium each containing N6 main Inorganic Salts diluted to 10%, 50% increased the transformation efficiencies to 4.0% and 17.5%, respectively (Vega et al. 2008: Non-Patent Document 15).

It is reported concerning wheat that a use of an *Agrobacterium* suspension medium and a co-cultivation medium each consisting of MS medium comprising inorganic salts diluted to 10% provided a significantly high rate of immature embryos exhibiting transient expression of GUS genes than the above medium consisting of a one-time amount of MS Inorganic Salts (Cheng et al. 1997: Non-Patent Document 16). As such, it is considered that "low inorganic salt mediums are generally used to improve the transient expression or transformation efficiency of the gene introduced to several major crops by *Agrobacterium* (Vega et al. 2008: Non-Patent Document 15)."

On the other hand, although not a co-cultivation medium, a use of a medium having an increased ammonium nitrate concentration as a pre-culture medium for the plant material of tobacco before inoculation with *Agrobacterium* was reported to have increased the transient expression of the introduced gene and the transformation efficiency (Boyko et al. 2009: Non-Patent Document 17). It is also reported that the transformation efficiency of *Arabidopsis* and tobacco increased by an addition of potassium chloride or a chloride of rare earth elements to the medium for pre-culture of plant tissues before inoculation with *Agrobacterium* (Boyko et al. 2011: Non-Patent Document 18).

There is also report of promoting a transient expression of introduced genes by adding antioxidant materials or copper to a co-cultivation medium. With regards to corn, it was reported that the transient expression of introduced gene and the transformation efficiency increased significantly when L-cysteine (0.4 g/L) and dithiothreitol (DTT) (0.4 g/L), which are anti-oxidant materials, were added to the MS medium, N6 medium, LS medium, and the D medium, relative to a plot where none was added (Non-Patent Document 14).

3. Medium Used in Plant Tissue Culture

In addition to the above MS medium (LS medium), mediums of various constitution are developed and used in culturing plant tissues.

The N6 medium was used mainly as another culture medium of rice. The B5 medium was developed for use in liquid culture, but it is also used as a solid medium in many plant cell cultures. The R2 medium is a medium based on the B5 medium and developed for use in suspension culture cells of rice. The CC medium was devised as a medium for forming callus from the protoplast of corn.

The following chart shows the total concentration of $NH_4^+$ and $NO_3^-$ as the nitrogen source and the concentrations of various inorganic ions (magnesium ion, potassium ion, calcium ion, and sodium ion) in the MS medium, LS medium, N6 medium, B5 medium, R2 medium and the CC medium.

TABLE 1

|  | MS | LS | N6 | B5 | R2 | CC |
|---|---|---|---|---|---|---|
| $NH_4^+$, $NO_3^-$ Total (mM) | 60.0 | 60.0 | 35.0 | 27.0 | 45.0 | 28.0 |
| $Mg^{2+}$ (mM) | 1.5 | 1.5 | 0.8 | 2.0 | 1.0 | 1.0 |
| $K^+$ (mM) | 20.0 | 20.0 | 30.9 | 25.0 | 40.0 | 13.0 |
| $Ca^{2+}$ (mM) | 3.0 | 3.0 | 1.1 | 1.0 | 1.0 | 4.0 |
| $Na^+$ (mM) | 0.0 | 0.0 | 0.0 | 1.1 | 2.0 | 0.0 |

PRIOR ART DOCUMENTS

Non-Patent Documents

Non-Patent Document 1: Hiei et al. (1994) The Plant Journal 6:271-282.
Non-Patent Document 2: Ishida et al. (1996) Nature Biotechnology 14:745-750.
Non-Patent Document 3: Cheng et al. (1997) Plant Physiol. 115: 971-980.
Non-Patent Document 4: Tingay et al. (1997) Plant J. 11: 1369-1376.
Non-Patent Document 5: Zhao et al. (2000) Plant Molecular Biology 44:789-798.
Non-Patent Document 6: Hiei et al. (2006) Plant Cell Tissue Organ Cult 87: 233-243.
Non-Patent Document 7: Gurel et al. (2009) Plant Cell Rep 28(3): 429-444.
Non-Patent Document 8: Cai et al. (1987) Plant Cell Tissue Organ Cult. 9:245-252.
Non-Patent Document 9: Elkonin et al. (1995) Maydica 40(2):153-157.
Non-Patent Document 10: Elkonin et al. (2000) Plant Cell Tissue Organ Cult 61(2):115-123.
Non-Patent Document 11: Gao et al. (2005) Genome 48:321-333.
Non-Patent Document 12: Wu et al. (2014) In Vitro Cell Dev Biol-Plant 50: 9-18.
Non-Patent Document 13: Guoquan et al. (2013) In Vitro Cell Dev. Biol-Plant 49(2):191-197.
Non-Patent Document 14: Du et al. (2010) African Journal of Biotechnology 9(8): 1135-1143.
Non-Patent Document 15: Vega et al. (2008) Plant Cell Reports 27(2): 297-305.
Non-Patent Document 16: Cheng et al. (1997) Plant Physiol Physiol 115: 971-980.
Non-Patent Document 17: Boyko et al. (2009) Plant Cell Reports 28: 737-757.
Non-Patent Document 18: Boyko et al. (2011) Plant Cell Reports 30: 505-518.

SUMMARY OF INVENTION

Technical Problem

It is an object of the present invention to provide a method of gene introduction into genus *Sorghum* plant and a method of producing a transformed genus *Sorghum* plant at a higher efficiency than conventionally known *Agrobacterium* methods.

Means to Solve the Problem

The present inventors worked diligently to solve the above problem, and consequently found that the gene introduction efficiency and the transformation efficiency can be improved in a genus *Sorghum* plant by using a medium having a higher concentration of the nitrogen source, and/or higher concentrations of inorganic ions selected from a magnesium ion, a potassium ion, a calcium ion and a sodium ion, compared to the medium with a one-time amount of LS Inorganic Salts.

The present invention is preferably accomplished by the embodiments described below, but is not limited thereto.

Embodiment 1

A method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in a presence of the *Agrobacterium*, wherein a medium with an increased concentration of magnesium ion is used in the steps (i), (ii) and/or (iii), and the magnesium ion concentration in the medium is 4.0 mM or higher and 100 mM or lower.

Embodiment 2

A method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in a presence of the *Agrobacterium*, wherein a medium with an increased concentration of a nitrogen source is used in the steps (i), (ii) and/or (iii), and a total concentration of $NH_4^+$ and $NO_3^-$ in the medium is higher than 60 mM and 270 mM or lower.

Embodiment 3

A method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in a presence of the *Agrobacterium*, wherein a medium with an increased concentration of a nitrogen source and/or magnesium ion is used in the steps (i), (ii) and/or (iii), and a total concentration of $NH_4^+$ and $NO_3^-$ in the medium is 60 mM or higher and 270 mM or lower, and the magnesium ion concentration in the medium is 2.6 mM or higher and 100 mM or lower.

Embodiment 4

A method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in a presence of the *Agrobacterium*, wherein a medium with an increased concentration of a nitrogen source and/or potassium ion is used in the steps (i), (ii) and/or and a total concentration of $NH_4^+$ and $NO_3^-$ in the medium is 60 mM or higher and 270 mM or lower, and the potassium ion concentration in the medium is 24 mM or higher and 65 mM or lower.

Embodiment 5

A method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in the presence of the *Agrobacterium*, wherein a medium with an increased concentration of a nitrogen source and/or calcium ion is used in the steps (i), (ii) and/or (iii), and a total concentration of $NH_4^+$ and $NO_3^-$ in the medium is 60 mM or higher and 270 mM or lower, and the calcium ion concentration in the medium is 5.2 mM or higher and 10 mM or lower.

Embodiment 6

A method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in the presence of the *Agrobacterium*, wherein a medium with an increased concentration of a nitrogen source and/or sodium ion is used in the steps (i), (ii) and/or (iii), and a total concentration of $NH_4^+$ and $NO_3^-$ in the medium is 60 mM or higher and 270 mM or lower, and the sodium ion concentration in the medium is 0.6 mM or higher and 200 mM or lower.

Embodiment 7

The method according to any one of Embodiments 1 to 6, wherein a medium with an increased concentration of a nitrogen source and/or an increased concentration of inorganic ions selected from magnesium ion, potassium ion, calcium ion and sodium ion, is used in at least the co-cultivation step (iii).

Embodiment 8

A method for producing a transformed genus *Sorghum* plant by performing steps (i) to (iii) according to the method of any one of Embodiments 1 to 7, further comprising:
(iv) a resting step of culturing the tissue cultured in the co-cultivation step in a resting medium; and
(v) a regeneration step of regenerating the tissue in a regeneration medium.

Embodiment 9

The method according to any one of Embodiments 1 to 8, further comprising at least one of the following treatments for transformation efficiency enhancement:

a) a thermal treatment;
b) a centrifugation treatment;
c) a pressurization treatment;
d) a treatment that uses a medium with an increased concentration of a metal salt including copper ion in step (ii) and/or (iii); and
e) a treatment that uses a medium with an increased concentration of silver nitrate in step (ii) and/or (iii).

Embodiment 10

The method according to either Embodiment 8 or 9, further comprising a selection step between the resting step (iv) and the regeneration step (v).

Embodiment 11

The method according to any one of Embodiments 1 to 10, wherein the *Agrobacterium* is a bacterium selected from the group consisting of LBA4404, EHA101, EHA105, AGL0, AGL1, and C58C1.

Embodiment 12

The method according to any one of Embodiments 1 to 11, wherein the genus *Sorghum* plant is *Sorghum bicolor*.

Advantageous Effect of Invention

The present invention made it possible to perform gene introduction into a genus *Sorghum* plant with a high efficiency. This further enabled a genus *Sorghum* plant to be transformed with a high efficiency. The method of the present invention also made it possible to obtain a transformed *Sorghum* plant at a reduced cost.

BEST MODE FOR CARRYING OUT THE INVENTION

The arrangement of the present invention is described in detail below without being limited thereby. Unless otherwise defined in the present specification, the scientific terms and technical terms used in relation to the present invention hold the meaning that is commonly understood by a person skilled in the art.

The present invention provides a method of gene introduction into a tissue of a plant material of a genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in a presence of the *Agrobacterium*, wherein a medium with an increased concentration of a nitrogen source and/or an increased concentration of inorganic ions is used in the steps (i), (ii) and/or (iii).

The present invention further provides a method for creating a transformed genus *Sorghum* plant, comprising:
(i) a step of preparing a plant material;
(ii) a step of inoculating a tissue of the plant material with *Agrobacterium*; and
(iii) a co-cultivation step of culturing the tissue inoculated with the *Agrobacterium* in a presence of the *Agrobacterium*;
(iv) a resting step of culturing the tissue cultured in the co-cultivation step in a resting medium; and
(v) a regeneration step of regenerating the tissue in a regeneration medium, wherein a medium with an increased concentration of a nitrogen source and/or an increased concentration of inorganic ions is used in the steps (i), (ii) and/or (iii).

The plant materials that can be used in the present invention are derived from a genus *Sorghum* plant. Note that the genus *Sorghum* is also referred to as the genus Morokoshi in Japanese, but the name "genus *Sorghum*" is uniformly used throughout the present specification. An example of a "genus *Sorghum*" plant in the present specification, without being limited thereby, is *Sorghum* bicolor.

*S. bicolor* is especially preferable in the present invention. Note that "*S. bicolor*" in the present specification refers to a specific species by the name of "*Sorghum*" in the "genus *Sorghum*." Furthermore, *S. bicolor* is also called Morokoshi, Takakibi, Gāoliáng, but they all refer to the same plant species, and these names may also be used in the present invention.

The "plant material" that may be used in the present invention encompasses various embodiments of a genus *Sorgham* plant, including but not limited to, the cell, leaf, root, stem, fruit, and other plant tissues of any section of the plant, an immature embryo, a mature seed, callus or an adventive embryo-like tissue (referred to hereinafter as "callus, etc." or simply "callus"), or a complete plant, which are provided for gene introduction or transformation of a plant by *Agrobacterium* method. A preferable form of the plant material used in the method of the present invention is an immature embryo, a mature seed, and a callus derived therefrom, of which an immature embryo is the most preferable.

Throughout the specification, the term "immature embryo" refers to an embryo of an immature seed during maturation after pollination. Any stage (maturing stage) of an immature embryo can be used in the method of the present invention without specific limitation, and the immature embryo may be harvested at any stage after pollination, and preferably on the 2nd day from pollination or later, more preferably on the 7th to 24th day from pollination. The immature embryo can be used on the day of isolation. Alternately, a pre-cultured immature embryo may be used.

Throughout the specification, the term "mature seed" refers to a fully-ripened seed after completion of maturation after pollination.

Throughout the specification, the term "callus" refers to an undifferentiated cell mass that grows randomly. Callus may be obtained by culturing differentiated cells of plant tissues in mediums (referred to as dedifferentiation medium) containing plant growth regulators such as auxin (e.g. 2,4-dichlorophenoxy acetate (2,4-D)), and cytokinin. The treatment to obtain callus is called a dedifferentiation treatment, and the step is called a dedifferentiation step.

In the method of the present invention, a medium with an increased concentration of a nitrogen source and/or an increased concentration of inorganic ions is a medium with a higher concentration of a nitrogen source and/or inorganic ions relative to the concentration of a nitrogen source and/or inorganic ions contained in the MS (LS) basic medium that is well known to a person skilled in the art. A high concentration is a concentration that is higher than that of a nitrogen source and/or inorganic ions contained in the MS (LS) basic medium (Zhao, et al., 2000: Non-Patent Document 5). Specifically, the MS (LS) basic medium contains $NH_4^+$ and $NO_3^-$ as the nitrogen source, and the total concentration thereof is 60.0 mM. Further, the MS (LS) basic medium contains 1.5 mM magnesium ion, 20.0 mM potassium ion, 3.0 mM calcium ion. The MS (LS) basic medium does not contain any sodium ion. If the medium contains a nitrogen source and/or inorganic ions of a higher concentration relative to the concentration of the nitrogen source and/or inorganic ions contained in these MS (LS) basic medium, the medium is a medium with an increased concentration of a nitrogen source and/or an increased concentration of inorganic ions.

In the method of the present invention, a medium with an increased concentration of a nitrogen source and/or an increased concentration of inorganic ions is used in at least one of the step of preparing a plant material (i), the step of inoculation with *Agrobacterium* (ii), and the co-cultivation step (iii). Preferably, the medium is used in at least the co-cultivation step (iii).

In one embodiment of the invention, the medium with an increased concentration of a nitrogen source and/or an increased concentration of inorganic ions is a medium with an increased concentration of magnesium ion. The magnesium ion concentration in the medium with the increased concentration of magnesium ion is 4.0 mM or higher and 100 mM or lower, preferably 4.8 mM or higher and 90.4 mM or lower. Or else, the lower limit of magnesium ion in this case may be selected from 4.0 mM or higher, 4.8 mM or higher, and 7.5 mM or higher, and the upper limit may be selected from 100 mM or lower, 90.4 mM or lower, 80 mM or lower, 70 mM or lower, 60 mM or lower, 50 mM or lower, 45.3 mM or lower, 40.0 mM or lower. The lower limit and upper limit of the magnesium ion concentration may be appropriately selected from the above values and combined.

In another embodiment of the invention, the medium with an increased concentration of a nitrogen source and/or an increased concentration of inorganic ions is a medium with an increased concentration of a nitrogen source. The total concentration of $NH_4^+$ and $NO_3^-$ in the medium with the increased concentration of the nitrogen source was higher than 60 mM and equal to or lower than 270 mM, preferably 62 mM or higher and 270 mM or lower. Or else, the lower limit of the total concentration of $NH_4^+$ and $NO_3^-$ in this case may be selected from higher than 60 mM, 62 mM or higher, 65 mM or higher, 70 mM or higher, 75 mM or higher, and 80 mM or higher, and the upper limit may be selected from 270 mM or lower, 263 mM or lower, 250 mM or lower, 225 mM or lower, 200 mM or lower, 175 mM or lower, 150 mM or lower, 125 mM or lower, 115 mM or lower and 112 mM or lower. The lower limit and upper limit of the total concentration of $NH_4^+$ and $NO_3^-$ may be appropriately selected from the above values and combined.

In a further embodiment of the invention, the medium with an increased concentration of a nitrogen source and/or an increased concentration of inorganic ions is a medium with an increased concentration of a nitrogen source and/or an increased concentration of a magnesium ion, potassium ion, calcium ion or sodium ion.

The total concentration of $NH_4^+$ and $NO_3^-$ in the medium with the increased concentration of the nitrogen source and/or the increased concentration of magnesium ion, potassium ion, calcium ion or sodium ion is 60 mM or higher and 270 mM or lower, preferably 62 mM or higher and 112 mM or lower. Or else, the lower limit of the total concentration of $NH_4^+$ and $NO_3^-$ in this case may be selected from 60 mM or higher, 62 mM or higher, 65 mM or higher, 70 mM or higher, 75 mM or higher, and 80 mM or higher, and the upper limit may be selected from 270 mM or lower, 263 mM or lower, 250 mM or lower, 225 mM or lower, 200 mM or lower, 175 mM or lower, 150 mM or lower, 125 mM or lower, 115 mM or lower and 112 mM or lower. The lower limit and upper limit of the total concentration of $NH_4^+$ and $NO_3^-$ may be appropriately selected from the above groups of values and combined.

The concentration of magnesium ion in the medium with the increased concentration of the nitrogen source and/or the increased concentration of magnesium ion is 2.6 mM or higher and 100 mM or lower, preferably 4.8 mM or higher and 90.4 mM or lower. Or else, the lower limit of magnesium ion concentration in this case may be selected from 2.6 mM or higher, 4.0 mM or higher, 4.8 mM or higher, and 10.0 mM or higher, and the upper limit may be selected from 100 mM or lower, 90.4 mM or lower, 80 mM or lower, 70 mM or lower, 60 mM or lower, 50 mM or lower, and 45.3 mM or lower. The lower limit and upper limit of the magnesium ion concentration may be appropriately selected from the above groups of values and combined.

The concentration of potassium ion in the medium with the increased concentration of the nitrogen source and/or the increased concentration of potassium ion is 24 mM or higher and 65 mM or lower, preferably 24 mM or higher and 60 mM or lower. Or else, the lower limit of potassium ion in this case may be selected from 24.0 mM or higher, 27.0 mM or higher, and 30 mM or higher, and the upper limit may be selected from 70 mM or lower, 65 mM or lower, 64.1 mM or lower, 60 mM or lower, 55 mM or lower, 50 mM or lower, and 45 mM or lower. The lower limit and upper limit of the potassium ion concentration may be appropriately selected from the above groups of values and combined.

The concentration of calcium ion in the medium with the increased concentration of the nitrogen source and/or the increased concentration of calcium ion is 5.2 mM or higher and 10 mM or lower, preferably 5.2 mM or higher and 9.6 mM or lower. Or else, the lower limit of calcium ion in this case may be selected from 5.2 mM or higher, 5.5 mM or higher, and 6.0 mM or higher, and the upper limit may be selected from 10 mM or lower, 9.6 mM or lower, 9.0 mM or lower, 8.0 mM or lower, 7.5 mM or lower, 7.0 mM or lower, and 6.9 mM or lower. The lower limit and upper limit of the calcium ion concentration may be appropriately selected from the above groups of values and combined.

The concentration of sodium ion in the medium with the increased concentration of the nitrogen source and/or the increased concentration of sodium ion is 0.6 mM or higher and 200 mM or lower, preferably 0.6 mM or higher and 150 mM or lower, more preferably 40.0 mM or higher and 50.0 mM or lower. Or else, the lower limit of sodium ion in this case may be selected from 0.6 mM or higher, 1.0 mM or higher, 4.0 mM or higher, 10.0 mM or higher, 20.0 mM or higher, 30.0 mM or higher and 40.0 mM or higher, and the upper limit may be selected from 200 mM or lower, 175 mM or lower, 150.1 mM or lower, 150 mM or lower, 125 mM or lower, 100 mM or lower, 90.1 mM or lower, 90 mM or lower, 80 mM or lower, 70 mM or lower, 60 mM or lower, and 50 mM or lower. The lower limit and upper limit of the sodium ion concentration may be appropriately selected from the above groups of values and combined.

Each step of the method of the present invention is described in detail below.

1. Steps of the Present Invention

The gene introduction method and the method of producing a transformed plant of the present invention uses *Agrobacterium*. Other than the steps otherwise indicated, the method may be carried out by steps of a publicly known gene introduction method or transformation method using *Agrobacterium*.

(i) Step of Preparing the Plant Material

In step (i), a plant material preferable for gene introduction or transformation is prepared by extracting plant material such as immature embryo or a mature seed from a plant or seeds, or by obtaining a callus derived therefrom as necessary. The definition of a "plant material" is as mentioned above. The plant material is prepared by isolating/collecting tissues from a genus *Sorghum* plant (including, but not limited to, immature embryo, mature seed). Further, a plant material may be prepared by deriving a callus from the isolated/collected tissue. The plant material may further be cultured before it is infected with *Agrobacterium* if desired.

The size of the plant material of the genus *Sorghum* plant used in the present invention is not particularly limited, but for instance, the immature embryo to be used may have a size of 1.0 to 3.0 mm.

In step (i), a medium with an increased concentration of nitrogen source and/or an increased concentration of inorganic ion may be used as mentioned above.

Further in step (i), various treatments for improving the transformation efficiency may be performed. Such treatments may include, for example, a thermal treatment, a centrifugation treatment, a thermal treatment and a centrifugation treatment, and a pressurization treatment. Treatments such as these for increasing transformation efficiency are described in detail in item 2. below.

(ii) Step of Inoculating a Tissue of the Plant Material with *Agrobacterium*

In step (ii), the tissue of a plant material of a genus *Sorghum* plant prepared in step (i) is inoculated with *Agrobacterium*.

Throughout the specification, the term "inoculation" refers to bringing *Agrobacterium* into contact with a tissue of a plant, and various methods for inoculation with *Agrobacterium* are known in the art. Examples of the method include a method comprising addition of a plant tissue to a suspension of *Agrobacterium* in a liquid medium, a method comprising direct dropwise addition of a suspension of *Agrobacterium* onto a plant tissue on a co-cultivation medium, a method comprising injection of a suspension of *Agrobacterium* into a plant tissue, and a method comprising immersion of a plant tissue in a suspension of *Agrobacterium* and a reduction of the pressure. In the present invention, however, the method of inoculation with *Agrobacterium* is not limited to these methods.

In the inoculation with *Agrobacterium*, in order to enhance the transformation efficiency by *Agrobacterium*, for example, various additives such as acetosyringone, a surfactant, or a porous ceramic may be added to the suspension of *Agrobacterium*.

Any known *Agrobacterium* can be used in transformation by *Agrobacterium* without limitation in the present invention. In a preferred embodiment of the present invention, *Agrobacterium* is *Agrobacterium tumefaciens*, such as LBA4404, EHA101, EHA105, AGL0, AGL1, or C58C1, but is not limited thereto.

*Agrobacterium* is known to have a property of introducing a gene inserted in T-DNA of a plasmid existing in the *Agrobacterium* into the genome of a plant. Thus, the *Agrobacterium* that can be used in the present invention has a plasmid where a gene to be expressed in a plant is inserted into T-DNA. A plant can be transformed through inoculation of a tissue of the plant with *Agrobacterium* having this plasmid. A desired characteristic can thereby be provided to the plant cells in the tissue. Examples of the plasmid for *Agrobacterium* that can be used in the present invention include, but is not limited to, pLC41, pSB131, U0009B, U0017S, pSB134, pNB131, and pIG121Hm.

A medium with an increased concentration of a nitrogen source and/or an increased concentration of inorganic ions may be used in step (ii) as shown above.

Further, in step (ii), various treatments for improving the transformation efficiency may be performed. Such treatments may include, for example, a thermal treatment, a centrifugation treatment, a thermal treatment and a centrifugation treatment, and a pressurization treatment, a treatment that uses a medium with an increased concentration of a metal salt including copper ion, and a treatment that uses a medium with an increased concentration of silver nitrate. Treatments such as these for increasing transformation efficiency are described in detail in item 2. below.

(iii) Co-Cultivation Step

In step (iii), a co-cultivation step is performed to culture a tissue of the plant material inoculated with *Agrobacterium* in step (ii) in the presence of *Agrobacterium*. The step ensures introduction of DNA from *Agrobacterium* into the plant cell by culturing the plant tissue inoculated with *Agrobacterium* under the coexistence of *Agrobacterium*.

The medium used in step (iii) is referred to as a "co-cultivation medium." The co-cultivation medium may be a medium that is commonly used to commonly culture plant cells, for example, a medium based on LS Inorganic Salts (Linsmaier, E., and Skoog, F., (1965) Physiol. Plant, 18:100-127). Preferably, in step (iii), a medium with an increased concentration of nitrogen source and/or an increased concentration of inorganic ions may be used as a co-cultivation medium.

In addition, 2,4-dichlorophenoxy acetate (2,4-D), picloram, dicamba or other auxins may be added to the co-cultivation medium used in the present invention. Or else, other plant growth regulators including cytokinin such as kinetin or 4PU may be added.

The term "culture" in this step refers to placing a plant tissue onto a solidified co-cultivation medium or in a liquid co-cultivation medium and then growing the tissue at an appropriate temperature, light-dark condition, and period. In the present invention, the medium can have any form that can sufficiently supply culture components to the plant tissue. The co-cultivation medium can be solidified with a gelling agent known in the art. A typical example of the gelling agent is agarose. The solidified co-cultivation medium can be suitably used in the present invention.

The culture temperature in this step (iii) can be appropriately selected and is preferably 18° C. to 30° C. and more preferably 25° C. The culture in this step (iii) is preferably performed in a dark place, although not limited thereto. The culture period in this step (iii) can be also appropriately selected and is preferably 1 to 7 days and more preferably 2 to 5 days. It is even more preferably 3 to 4 days.

When an immature embryo is used as the plant material, the immature embryo can be cultured in step (iii) of the present invention by being placed in such a manner that the scutellum side faces upward while the embryonic axis side is in contact with the medium, or in such a manner that the embryonic axis side faces upward while the scutellum side faces downward and is in contact with the medium. The immature embryo is preferably co-cultivated by being placed in such a manner that the scutellum side faces upward while the embryonic axis side is in contact with the medium.

Further, in step (iii), various treatments for improving the transformation efficiency may be performed. Such treatments may include, for example, a centrifugation treatment, a pressurization treatment, a treatment that uses a medium with an increased concentration of a metal salt including copper ion, and a treatment that uses a medium with an increased concentration of silver nitrate. Treatments such as these for increasing transformation efficiency are described in detail in item 2. below.

(iv) Resting Step

The method of producing a transformed plant of the present invention further involves a resting step and a regeneration step after the co-cultivation step to produce a transformed plant.

In the resting step (iv), the plant tissue is cultured with a resting medium after the co-cultivation step. This step removes *Agrobacterium* from the plant cells after the co-cultivation step and also proliferates the plant cells.

The medium used in this step is referred to as a "resting medium" throughout the specification. The resting medium may be any medium that is usually used for culturing plant cells, and examples thereof include medium based on LS Inorganic Salts or N6 Inorganic Salts (Chu, C.-C., (1978) Proc. Symp. Plant Tissue Culture, Peking: Science Press, pp. 43-50). The resting medium in this step preferably contains an antibiotic. The antibiotic contained in the resting medium differs from that used in the selection step described below and is used for eradicating *Agrobacterium*. Cefotaxime and/or carbenicillin, Timentin is, but not limited to, preferably used as the antibiotic.

The resting medium used in this step preferably contains a plant growth regulator. The plant growth regulator is preferably picloram and/or 2,4-D, or dicamba belonging to auxin. Since auxins can generally dedifferentiate plant tissues, almost all plant tissues are partially or completely converted to dedifferentiated tissues (callus) in this step (iv) and the subsequent selection step. Throughout the specification, the terms "dedifferentiated tissue" and "callus" refer to a tissue that is obtained by culturing a part (explant) of the differentiated plant tissue in a medium containing a plant growth regulator such as an auxin or a cytokinin and is amorphous and undifferentiated cell aggregation not having the shape of the original plant tissue. Accordingly, all embodiments relating to dedifferentiated tissues, for example, a case of subjecting a dedifferentiated tissue to the resting step and a case of completely or partially dedifferentiating a differentiated plant tissue in the resting step or in the subsequent selection step, are within the scope of the present invention.

Furthermore, the resting medium preferably includes saccharides. The source of saccharide may be sugar such as sucrose, glucose, maltose or sugar alcohol such as mannitol, sorbitol. Although it does not relate to genus *Sorghum*, there is a report concerning rice that the production of callus and the regeneration efficiency improved by changing the sucrose concentration or the concentration of mannitol or sorbitol (Kavi Kishor (1987) Plant Science 48:189-194). The type and concentration of the saccharide source may also be changed appropriately in *Sorghum*.

The term "culture" in this step (iv) refers to placing a plant tissue onto a solidified resting medium or in a liquid resting medium and then growing the tissue at an appropriate temperature, light-dark condition, and period. In the present invention, the medium can have any form that ensures sufficient supply of the medium components to a plant tissue. The resting medium can be solidified with a gelling agent known in the art. A typical example of the gelling agent is agarose. The culture temperature in this step can be appropriately selected and is preferably 20° C. to 35° C. and more preferably 25° C. The culture in this step is preferably performed in a dark place, although not limited thereto. The culture period in this step can be also appropriately selected and is preferably 1 to 28 days and more preferably 7 to 21 days.

Further, in step (iv), various treatments for improving the transformation efficiency may be performed. Such treatments may include, for example, a centrifugation treatment, a pressurization treatment, a treatment that uses a medium with L-proline and/or L-asparagine added thereto (Elkonin, et al., 1995: Non-Patent Document 9), a medium with increased concentration of nitrate ions and phosphate ions (Elkonin, et al., 2000: Non-Patent Document 10), a medium with polyvinyl polyproline (PVPP) added thereto (Gao, et al., 2005: Non-Patent Document 11), and a medium with 6-benzylamino proline (BAP) (Wu, et al., 2014: Non-Patent Document 12) as the resting medium. Treatments such as these for increasing transformation efficiency are described in detail in item 2. below.

Further, a selection step may be performed in between the resting step (iv) and the regeneration step (v). The selection step is generally performed in transformation of a plant by *Agrobacterium*. The selection step is not indispensable in the method of producing a transformed plant of the present invention. For example, a desired transformant can be obtained through a transformation-improving treatment as described below without performing the selection step. The following description on the selection step is merely for exemplification, and the present invention is not limited to the following description.

In this step, a transformant is selected from the tissue obtained in the above-described steps based on whether a gene is introduced or not. The medium that is used in this step is referred to as "selection medium" throughout the specification. Examples of a selection medium that can be used include medium based on LS Inorganic Salts or N6 Inorganic Salts, for example, specifically MS medium.

In a typical method of transformation using *Agrobacterium*, the selection medium contains an auxin, preferably 2,4-D and/or picloram, dicamba. The selection medium in a preferred embodiment of the present invention similarly contains a plant growth regulator. Any auxin can be used in this selection step without limitation and preferred is 2,4-D. Furthermore, the selection medium may contain various optional additives.

The transformed plant can be selected by, for example, culturing the plant subjected to the co-cultivation step and/or the resting step in a selection medium containing an appropriate selective agent and selecting one having resistance to the selective agent. Any selective agent that is usually used in the art can be used in this step. For example, an antibiotic or an herbicide can be used as the selective agent. Examples of the antibiotic include hygromycin, kanamycin, and blasticidin S, and examples of the herbicide include phosphinothricin, bialaphos, and glyphosate.

In order to perform the selection step, DNA inserted into T-DNA in *Agrobacterium* must include not only the gene to be expressed in the plant but also, for example, a resistance gene against the selective agent. The resistance gene against the selective agent is known in the art. In this step, for example, if the selection is performed with a selection medium containing hygromycin, a gene to be expressed in a plant and a hygromycin resistance gene must be introduced in the plant.

Alternatively, a transformed plant can be selected on the basis of the sugar requirement of plant cells. With sugars assimilable by plant cells, it is known that the plant cell can assimilate sucrose and glucose but not mannose. If a plant tissue is cultured in a medium containing mannose as a main carbon source, the plant tissue dies or does not grow due to the deficiency or lack of assimilable sugar. Selection based on the sugar requirement utilizes this principle. That is, in order to perform this selection process, DNA inserted into T-DNA in *Agrobacterium* must include not only a gene to be expressed in a plant but also a phosphomannose isomerase (PMI) gene. In this case, plant cells containing an introduced PMI gene acquire an ability to assimilate mannose as a carbon source. As a result, only a plant tissue transformed with *Agrobacterium* as described above can grow on a medium containing mannose as a main carbon source, whereby only the transformed plant tissue can be selected (Negrotto, D., et al., (2000) Plant Cell Reports, 19:798-803). Such a method is also applicable to other sugars. For example, plant cells containing an introduced xylose isomerase gene can utilize xylose as a carbon source and can be therefore applied to such a method.

Alternatively, a readily detectable gene may be introduced as a screening marker to select a transformed plant on the basis of the expression of this gene. Examples of such a gene serving as a screening marker include a GFP gene. Methods for detecting cells or tissues expressing such a gene are known in the art.

This step may be repeated multiple times with medium having different compositions. For example, repeating the selection step multiple times with an increased concentration of selective agent at every selection step enhances the reliability of selection by the agent and the probability of obtaining a transformed plant. The selection step is preferably performed at least once and more preferably twice, and even more preferably three times. In the case of multiple selection steps, a transformed tissue can also be efficiently acquired by excising the proliferated portion from the tissue cultured in the medium containing the selective agent and subjecting only the proliferated portion to the subsequent selection step.

The term "culture" in this step refers to placing a plant tissue onto a solidified selection medium or in a liquid selection medium and then growing the tissue at an appropriate temperature, light-dark condition, and period. In the present invention, the medium may have any form that allows the medium components to be sufficiently supplied to a plant tissue. The selection medium can be solidified with, for example, agarose, as described above. The culture temperature in this step can be appropriately selected and is preferably 20° C. to 35° C. and more preferably 25° C. The culture in this step is preferably performed in a dark place, although not limited thereto. The culture period in this step can be also appropriately selected. For example, in the case of repeating the selection step twice, the culture is performed for three weeks in total, that is, one week for the primary selection and two weeks for the secondary selection. In the case of multiple selection steps, the culture is performed preferably for two to eight weeks, and more preferably three to six weeks, in total. In the multiple selection steps, the culture period, the culture temperature, and light-dark condition may be varied at every selection step.

(5) Regeneration Step

In step (v), the tissue cultured in the resting medium is, through optional selection, regenerated in a regeneration medium. The medium used in this step is referred to as "regeneration medium" throughout the specification. The regeneration medium may contain auxin or cytokinin as necessary.

Examples of a regeneration medium that can be used include medium based on LS Inorganic Salts or N6 Inorganic Salts, for example, specifically MS medium.

The regeneration medium may contain a selective agent. Though the selective agent that can be used in this step is the same as that defined in the selection step, the selective agent used in this step does not necessarily have to be the same as that used in the selection step. In such a case, resistance genes against two or more selective agents must be introduced to the plant from *Agrobacterium*.

The term "regeneration" in the present invention indicates that a completely or partially dedifferentiated plant tissue acquires the properties of the original plant tissue or plant again. If an auxin is used in the co-cultivation step and/or the selection step, the plant tissue is completely or partially dedifferentiated. Accordingly, the dedifferentiated tissue is regenerated by subjecting the tissue to this step to obtain an intact transformed plant.

The term "culture" in this step refers to placing a plant tissue onto a solidified regeneration medium or in a liquid regeneration medium and then growing the tissue at an appropriate temperature, light-dark condition, and period. In the present invention, the medium may have any form that allows the medium components to be sufficiently supplied to a plant tissue. The regeneration medium can be solidified with, for example, agarose as described above. The culture temperature in this step can be appropriately selected and is preferably 20° C. to 35° C. and more preferably 25° C. The culture in this step is preferably performed under a bright condition for 16 to 24 hours per day, but is not limited thereto. The culture period in this step can be also appropriately selected and is preferably 7 to 56 days and more preferably 14 to 42 days.

Also in the regeneration step (v), various treatments to enhance the transformation efficiency may be performed. Such treatment includes using MS medium containing 1 mg/L NAA, 1 mg/L IAA, 1 mg/L IBA, 1 μmol/L copper sulfate (Non-Patent Document 13), or modified MS medium containing 0.5 mg/L zeatin, 1 mg/L indole-3-acetic acid (IAA), 0.1 mg/L thidiazuron (Non-Patent Document 12) as the regeneration medium. Treatments such as these for increasing transformation efficiency are described in detail in item 2. below.

2. Treatments for Transformation Efficiency Enhancement

The method of gene introduction and the method of production of a transformed plant of the present invention may include treatment for transformation efficiency enhancement described below. Throughout the specification, the term "treatments for transformation efficiency enhancement" represents a treatment for achieving an enhancement in transformation efficiency. Furthermore, the idea of "treatments for transformation efficiency enhancement" throughout the specification encompasses a treatment to enhance gene-introduction efficiency, a treatment to enhance callus-formation rate, and/or a treatment to enhance regeneration efficiency.

Treatments for transformation efficiency enhancement include one of the treatments in a) to k) below or a combination thereof without being limited thereby.

a) Thermal treatment;
b) Centrifugation treatment;
c) Pressurization treatment;
d) Thermal treatment and centrifugation treatment;
e) A treatment that uses a medium with an increased concentration of a metal salt including copper ion during inoculation with *Agrobacterium* and/or a co-cultivation step;
f) A treatment that uses a medium with an increased concentration of silver nitrate during inoculation with *Agrobacterium* and/or a co-cultivation step;

g) A treatment that uses a medium with L-proline and/or L-asparagine added thereto in the resting step;
h) A treatment that uses a medium with an increased concentration of nitrate ions and phosphate ions in the resting step;
i) A treatment that uses a medium with polyvinyl pyrrolidone (PVPP) added thereto in the resting step;
j) A treatment that uses a medium with 6-benzylamino proline (BAP) in the resting step or regeneration step; and
k) A treatment that uses MS medium containing 1 mg/L naphthaleneacetic acid (NAA), 1 mg/L indole-3-acetic acid (IAA), 1 mg/L indole-3-butyric acid (IBA) and 1 μmol/L copper sulfate in the regeneration step; and
l) A treatment that uses modified MS medium containing 0.5 mg/L zeatin, 1 mg/L indole-3-acetic acid (IAA), 0.1 mg/L thidiazuron in the regeneration step.

Of treatments a) to k) above, a) to e) have the effect of enhancing gene-introduction efficiency, b), e) to i) have the effect of enhancing the callus-formation rate, and e), h) and k) have the effect of enhancing the regeneration efficiency. Although it has not yet been confirmed which of the stages of gene-introduction efficiency, callus-formation rate or regeneration efficiency j) was effective in, it enhances the transformation efficiency as a result. In an embodiment of the present invention, treatment j) does not necessarily have to be incorporated in the method of the present invention. In another embodiment of the present invention, the treatment j) is performed in the regeneration step in a method of the present invention.

The thermal treatment may be performed, for example, by the method described in WO 1998/054961. The thermal treatment may be performed in step (i) or (ii) of the present invention. For example, when a thermal treatment is performed before bringing the plant material in contact with *Agrobacterium*, the treatment is performed at a temperature of from 33° C. to 60° C., preferably 37° C. to 52° C., for the period of from 5 sec. to 24 h., preferably 1 min. to 24 h.

The centrifugation treatment may be performed, for example, by the method described in WO 2002/012520. The centrifugation treatment may be performed in any of steps (i) to (iv) of the present invention. The condition for performing a centrifugation treatment before bringing a plant material in contact with *Agrobacterium* may be a treatment at a centrifugal acceleration of 100 G to 250,000 G, preferably 500 G to 200,000 G, more preferably 1,000 G to 150,000 G and a period of 1 sec. to 4 h., more preferably 1 sec. to 2 h. Further, the condition for performing the centrifugation treatment after the co-cultivation step may be a treatment in a centrifugal acceleration range of 100 G to 250,000 G, 500 G to 200,000 G, preferably 1,000 G to 150,000 G, most preferably 1,100 to 110,000 G and a period of 1 sec. or higher, preferably 1 sec. to 4 h., more preferably 1 sec. to 2 h., and even more preferably 1 sec. to 10 min. The time of the centrifugation treatment may be selected as necessary according to the centrifugal acceleration. The gene-introduction efficiency may be significantly enhanced even for a centrifugation treatment of an extremely short period, such as 1 sec. or lower, when the centrifugal acceleration is large. On the other hand, the centrifugation treatment may be performed extensively to significantly enhance the gene-introduction efficiency when the centrifugal acceleration is small. Note that an appropriate centrifugation treatment condition may be set readily by a routine experiment.

The pressurization treatment may be performed, for example, by the method described in WO 2005/017169. The treatment may be performed in any of steps (i) to (iv) of the present invention. The pressurization treatment is performed in a range of from 1.7 atm to 10 atm, more preferably from 2.4 atm to 8 atm without being limited thereby.

The thermal treatment and the centrifugation treatment may be performed, for example, by the methods described in WO 2002/012521. The conditions described above concerning the thermal treatment and the centrifugation treatment may be adopted as the conditions of the thermal treatment and the centrifugation treatment.

The treatment that uses a medium with an increased concentration of a metal salt including copper ion during inoculation with *Agrobacterium* and/or a co-cultivation step may be performed, for example, by the methods described in WO 2005/017152. The treatment may be performed in step (ii) or (iii) of the present invention. The treatment may be performed using a medium including a metal salt including copper ion in a concentration of 1 μM to 50 μM, preferably 1 μM to 10 μM. The metal salt may be, for example, copper sulfate or copper gluconate.

The treatment that uses a medium with increased concentration of silver nitrate during inoculation with *Agrobacterium* and/or a co-cultivation step may be performed, for example, by the methods described in Zhao, Z.-Y., et al., (2001) Mol. Breed., 8:323-333; Non-Patent Document 2; and/or Ishida, Y., et al., (2003) Plant Biotechnology, 20:57-66. The treatment may be performed in step (ii) or (iii) of the present invention. The treatment may be performed using a medium including silver nitrate in a concentration of 1 μM to 50 μM, preferably 1 μM to 10 μM.

The treatment that uses a medium with L-proline and/or L-asparagine added thereto, the treatment that uses a medium with an increased concentration of nitrate ions and phosphate ions in the resting step, the treatment that uses a medium with polyvinyl pyrrolidone (PVPP) added thereto, and the treatment that uses a medium with 6-benzylamino proline (BAP) in the resting step may be respectively performed, for example, by the methods described in Non-Patent Documents 9, 10, 11 and 12. The treatment may be performed in step (iv) of the present invention. The amount of the substance to be added may be determined as necessary by a person skilled in the art referring to the above Non-Patent Documents shown above.

The treatment that uses MS medium containing 1 mg/L NAA, 1 mg/L IAA, 1 mg/L IBA and 1 μmol/L copper sulfate in the regeneration step may be performed, for example, by the methods described in Non-Patent Document 13. Also, the treatment that uses modified MS medium containing 0.5 mg/L zeatin, 1 mg/L indole-3-acetic acid (IAA), 0.1 mg/L thidiazuron in the regeneration step may be performed, for example, by the methods described in Non-Patent Document 12. The treatment may be performed in step (v) of the present invention.

The person skilled in the art may perform the treatments for transformation efficiency enhancement at a suitable timing/condition. It is all the more preferable for the sake of transformation efficiency enhancement to combine them as necessary.

3. Effects of the Method of the Present Invention and Confirmation Methods Thereof Transformation in the present specification is a step of obtaining a plant in which the introduced target gene is incorporated into the nuclear genome and stably expressed. Through the method for producing a transformed plant of the present invention, it is possible to perform transformation of the genus *Sorghum* plant at a high efficiency. The transformation efficiency enhancement of plants is thus achieved.

The transformation step specifically goes through the steps of introduction of a target gene into the cells of the subject plant, callus formation from the tissue containing a cell to which a gene is introduced, and regeneration of callus comprising a gene introduced into a nuclear genome.

Throughout the specification, gene-introduction refers to an introduction of a target gene into the cell of the subject plant. The gene introduction method of the present invention enables a highly efficient gene introduction into a genus *Sorghum* plant. This also enables a transformed genus *Sorghum* plant to be produced at a high efficiency.

It is also possible to enhance the plant transformation efficiency by the improvement of the callus formation rate or the regeneration efficiency.

In other words, "a high transformation efficiency" is an idea encompassing the introduction of the target gene into the plant cell at a high efficiency (a high gene-introduction efficiency), a callus formation at a high efficiency from a plant tissue to which the target gene is introduced (a high callus-formation efficiency), a regeneration at a high efficiency from a callus in which the target gene is introduced (a high regeneration efficiency) throughout the specification. Further, throughout the specification, "a transformation efficiency enhancement" is an enhancement in the introduction efficiency of the target gene into the plant cell, an enhancement in the callus formation rate from the plant tissue to which the target gene is introduced, and an enhancement in the regeneration efficiency from the callus to which the target gene is introduced.

Advantageous effects may be obtained, such as a high reproducibility of the plant transformation efficiency, a low variability in transformation efficiency by experiment, and an acquisition of a stable transformed plant, based on the method for producing a transformed plant of the present invention. These effects are encompassed in the above idea of "a high transformation efficiency" or "a transformation efficiency enhancement" in a broad sense.

More reliable methods for determining if the subject plant was transformed are, for example, the southern hybridization method and PCR, which are used to confirm an incorporation of the introduced gene into the plant chromosome, and to confirm the expression of an introduced gene in a progeny plant (heredity of progeny). The southern hybridization or PCR may be performed by a well known method, and they may be performed, for example, by methods described in Sambrook, J., et al., Molecular Cloning: A Laboratory Manual, 3rd ed. (2001, Cold Spring Harbor Laboratory Press, Cold Spring Harbor, N.Y.). Further, a confirmation of expression in a progeny plant may be performed by a method for investigating the expression of a reporter gene such as a GUS gene or an expression of a selection marker gene such as a herbicide resistance gene. Details are provided in Non-Patent Document 2 without being limited thereby.

It can be determined if the gene introduction into a plant cell was performed by observing a transient expression of a gene-introduced tissue. A transient expression is a phenomenon in which a target gene that had transitioned into the nucleus of the plant cell expresses itself for a certain period using the protein expression mechanism of a plant cell. After the transient expression of the gene, a part of the target gene that had transitioned into the nucleus is incorporated into the nuclear genome, and the cell that incorporated the target gene starts stably expressing the target gene as a transformed cell.

The transient expression may be confirmed by various known methods. For example, reporter genes such as the GUS ($\beta$-glucuronidase) gene, a luciferase gene or a GFP gene may be used as the gene to be introduced, and the expression plots of these reporter genes may be confirmed by vision by using a simple, commonly known method.

The gene introduction efficiency may be evaluated by scoring the transient expression by vision at each stage. For example, the expression of the GUS gene in the scutellum tissue of the immature embryo may be evaluated in six grades in the resting step: an immature embryo with zero blue spot is scored 0, an immature embryo with 1 to 10 blue spots is scored 1, an immature embryo with 11 to 40 blue spots is scored 2, an immature embryo with 41 spots to less than one third of the scutellum is scored 3, and an immature embryo with one third or more and less than one half of the scutellum exhibiting blue is scored 4, and an immature embryo with one half or more of the scutellum exhibiting blue may be scored 5.

The gene-introduction efficiency may be determined by the calculation method commonly used by a person skilled in the art. For example, the gene introduction efficiency could be calculated by dividing the number of plant tissues to which gene was introduced with the number of plant tissues inoculated with *Agrobacterium*.

With regards to the callus formation rate, callus formation may be visually confirmed at each stage, and the average of callus formation of those stages may be taken. For example, the callus formation from an immature embryo may be evaluated in three grades of 1 (more than half of the scutellum forms a callus), 0.5 (a part of the scutellum forms a callus), and 0 (no callus is formed) as shown in the Examples shown below (the callus formation index in the Examples shown below). Or else, the callus formation rate may be calculated by dividing the number of callus formed by the number of plant tissues inoculated with *Agrobacterium*.

EXAMPLES

The present invention will now be described with reference to examples below, which are not intended to limit the technical scope of the invention. The scope of the present invention is defined by the appended claims. Based on description in the specification, modifications and changes will be apparent to those skilled in the art.

Example 1: Effect of High Nitrogen Co-Cultivation Medium on Gene Introduction Efficiency Materials and Methods The immature embryo of *Sorghum* 14 to 23 days after blooming (variety: Tx430) was aseptically collected and washed once with an *Agrobacterium* suspension medium (LS Inorganic Salts, 0.5 mg/L nicotinic acid, 0.5 mg/L pyridoxine hydrochloride, 1 mg/L thiamine hydrochloride, 100 mg/L myo-inositol, 1 g/L casamino acid, 1.5 mg/L 2,4-dichlorophenoxyacetic acid (2,4-D), 68.5 g/L sucrose, 36 g/L glucose, pH 5.2; Non-Patent Document 5). Pretreatment (15,000 rpm (20,000×g), a centrifugation treatment of 10 min. and a thermal treatment of 43° C., 3 min.) for increasing the gene introduction efficiency was performed. About $1.0 \times 10^9$ cfu/mL of *Agrobacterium* was suspended in the *Agrobacterium* suspension medium containing 100 μm of acetosyringone to from an inoculation source. Used as the *Agrobacterium* strain was EHA105 (pLC41 GUS-Bar:: pVGW7) having a binary vector which the T-DNA region of pLC41GWH (Pubi-lubi-IGUS-Tnos) described in WO 2014/157541 A1 is modified to a T-DNA having a GUS gene with which a catalase intron of *Ricinus communis* is intervened and controlled by a corn ubiquitin promoter and intron, and, a Bar gene controlled by a cauliflower mosaic virus 35S promoter (P35S-bar-T35S), as well as a booster vector described in WO 2014/157541 A1. The inoculation source was added to the pretreated immature embryo, and placed stationary at room temperature for 5 min. Immature embryos inoculated with *Agrobacterium* were placed on a co-cultivation medium containing a one-time amount of LS Inorganic Salts (LS Inorganic salt, 0.5 mg/L nicotinic acid, 0.5 mg/L pyridoxine hydrochloride, 1 mg/L thiamine hydrochloride, 100 mg/L myo-inositol, 700 mg/L L-proline, 1.5 mg/L 2,4-D, 20 g/L sucrose, 10 g/L glucose, 500 mg/L MES, 100 μM acetosyringone, 5 μM $AgNO_3$, 5 μM $CuSO_4.5H_2O$, 8 g/L agar, pH 5.8; refer to Non-Patent Document 5, ascorbic acid is excluded) or a co-cultivation medium comprising $NH_4^+$ and $NO_3^-$ at a total concentration of 22-362 mM, and other LS Inorganic Salts at a one fifth concentration, in such a manner that the scutellum side faces upward. The medium comprising $NH_4^+$ and $NO_3^-$ at a total concentration of 22-362 mM was adjusted by adding $NH_4NO_3$. Immature embryos cultured at 25° C. in the dark for 2 days were placed in a resting medium (LS Inorganic salt, 0.5 mg/L nicotinic acid, 0.5 mg/L pyridoxine hydrochloride, 1 mg/L thiamine hydrochloride, 100 mg/L myo-inositol, 1 g/L casamino acid, 3 mg/L 2,4-D, 30 g/L maltose, 7.5 g/L sorbitol, 7.8 μM $CuSO_4.H_2O$, 150 mg/L timentin, 3.5 g/L gellan gum, pH 5.8), and they were cultured at 25° C. in the dark.

The immature embryos were cultured for 3 days after being placed on the resting medium and were then washed once in a 0.1 M phosphate buffer solution (pH 6.8) containing 0.1% of Triton X-100 and immersed in a phosphate buffer solution containing 1.0 mM 5-bromo-4-chloro-3-indolyl-β-D-glucuronic acid (X-gluc). After reaction at 28° C. for 24 hours, the immature embryos were observed under a microscope to investigate the range of scutellum tissue that turns blue. Immature embryos with 0 spot turning blue was scored 0, those with 1 to 10 spots turning blue were scored 1, those with 11 to 40 spots turning blue were scored 2, those with 41 or more spots and less than one third of the scutellum turning blue were scored 3, those with one third or more and less than one half of the scutellum turning blue were scored 4, and those with one half or more scutellum turning blue were scored 5. Six to eight immature embryos were used for each experimental plot, and the test was performed twice.

Results

The average score of the transient expression of a GUS gene was higher when a co-cultivation medium comprising $NH_4^+$ and $NO_3^-$ at a total concentration of 62 mM-262.1 mM, and other LS Inorganic Salts at a one fifth concentration was used (Experimental plots 3 to 5) than when the control medium which is a co-cultivation medium containing LS Inorganic Salts at a one-time amount (controlplot) was used. It was thus confirmed that the introduction efficiency of an exogenous gene to a *Sorghum* immature embryo was enhanced by using a medium comprising $NH_4^+$ and $NO_3^-$ at a total concentration of 62 mM-262.1 mM, even in a low inorganic salt medium.

TABLE 2

| Co-cultivation Medium | Experimental Plot 1 | Control Plot | Experimental Plot 2 | Experimental Plot 3 | Experimental Plot 4 | Experimental Plot 5 | Experimental Plot 6 |
|---|---|---|---|---|---|---|---|
| N concentration (mM) | 12.0 ⅕ × LS | 60.0 1 × LS | 22.0 | 62.0 | 112.0 | 262.1 | 362.1 |
| GUS transient expression average score | 0 | 0.38 | 0.19 | 0.56 | 0.56 | 0.50 | 0.06 |

Example 2: Effect of High $Mg^{2+}$ Co-Cultivation Medium in Gene Introduction

Materials and Methods

Immature embryos treated similarly to Example 1 were placed on the control co-cultivation medium containing a one-time amount of LS Inorganic salt or experimental plot co-cultivation mediums comprising $Mg^{2+}$ at a concentration of 0.6-150.4 mM, and other LS Inorganic Salts at a one fifth concentration, and the transient expression of GUS genes was thus evaluated. The medium comprising $Mg^{2+}$ at a concentration of 0.6-150.4 mM was adjusted by adding $MgSO_4$. Six to seven immature embryos were used for each experimental plot, and the test was performed twice.

Results

The average score of GUS transient expression was higher when the $Mg^{2+}$ concentration was 4.8 mM-90.4 mM in the experimental plot mediums with an increased concentration of $Mg^{2+}$ than in the control medium (Experimental Plots 9 to 11). It was thus confirmed that the introduction efficiency of an exogenous gene to a *Sorghum* immature embryo was enhanced by a high $Mg^{2+}$ co-cultivation medium.

TABLE 3

| Co-cultivation Medium | Control Plot | Experimental Plot 7 | Experimental Plot 8 | Experimental Plot 9 | Experimental Plot 10 | Experimental Plot 11 | Experimental Plot 12 |
|---|---|---|---|---|---|---|---|
| $Mg^{2+}$ concentration (mM) | 1.5 1 × LS | 0.6 | 1.8 | 4.8 | 45.3 | 90.4 | 150.4 |
| GUS transient expression average score | 0.08 | 0.08 | 0.08 | 0.15 | 1.85 | 1.38 | 0.08 |

Example 3: Effect of High $Mg^{2+}$ and High N Co-Cultivation Medium in Gene

Materials and Methods

Immature embryos treated similarly to Example 1 were placed on the control co-cultivation medium containing a one-time amount of LS Inorganic Salts or experimental plot co-cultivation mediums comprising $Mg^{2+}$ at a concentration of 0.6-150.4 mM, $NH_4^+$ and $NO_3^-$ at a total concentration of 62.0 mM, and other LS Inorganic Salts at a one fifth concentration, and the transient expression of GUS genes was thus evaluated. The medium comprising $Mg^{2+}$ at a concentration of 0.6-150.4 mM was adjusted and prepared by adding $MgSO_4$, the medium comprising $NH_4^+$ and $NO_3^-$ at a total concentration of 62.0 mM was adjusted and prepared by adding $NH_4NO_3$. Eight immature embryos were used for each experimental plot, and the test was performed twice.

Results

The average score of GUS transient expression was significantly higher when the $Mg^{2+}$ concentration was 2.6 mM-90.4 mM in the experimental plot co-cultivation mediums with a high nitrogen condition than in the control medium (Experimental Plots 14 to 17). It was thus confirmed that the introduction efficiency of an exogenous gene to a Sorghum immature embryo was significantly enhanced by a high $Mg^{2+}$ high N co-cultivation medium.

TABLE 4

| Co-cultivation Medium | Control Plot | Experimental Plot 13 | Experimental Plot 14 | Experimental Plot 15 | Experimental Plot 16 | Experimental Plot 17 | Experimental Plot 18 |
|---|---|---|---|---|---|---|---|
| $Mg^{2+}$ concentration (mM) | 1.5 1 × LS | 0.6 | 2.6 | 4.8 | 45.3 | 90.4 | 150.4 |
| GUS transient expression average score | 0.08 | 0.15 | 0.62 | 0.58 | 3.00 | 1.54 | 0.08 |

Example 4: Effect of High $K^+$ and/or High N Co-Cultivation Medium in Gene Introduction Materials and Methods Immature embryos treated similarly to Example 1 were placed on the control co-cultivation medium containing a one-time amount of LS Inorganic salt or co-cultivation mediums comprising $K^+$ at a concentration of 8.0-204.4 mM, and other LS Inorganic Salts at a one fifth concentration, or co-cultivation mediums of LS Inorganic Salts at a one fifth concentration comprising the above $K^+$ as well as $NH_4^+$ and $NO_3^-$ at a total concentration of 62.0 mM, and the transient expression of GUS genes was thus evaluated. The medium comprising $K^+$ at a concentration of 8.0-204.4 mM was adjusted and prepared by adding $K_2SO_4$. Six to seven immature embryos were used for each experimental plot, and the test was performed four times.

Results

The average score of GUS transient expression was significantly higher when the $K^+$ concentration was 24.0 mM-64.1 mM in the experimental plot co-cultivation mediums with a high nitrogen condition than in the control medium (Experimental Plots 20, 21). It was thus confirmed that the introduction efficiency of an exogenous gene to a Sorghum immature embryo was enhanced by a high $K^+$ high N co-cultivation medium.

TABLE 5

| Co-cultivation Medium | | Control Plot | Experimental Plot 19 | Experimental Plot 20 | Experimental Plot 21 | Experimental Plot 22 |
|---|---|---|---|---|---|---|
| $K^+$ Concentration (mM) | | 20.0 1 × LS | 8.0 | 24.0 | 64.1 | 204.4 |
| GUS transient expression average score | $K^+$ | 0.13 | 0.06 | 0.19 | 0.19 | 0 |
| | $K^+$ + N | | 0.06 | 1.31 | 1.50 | 0.06 |

Example 5: Effect of High $Ca^{2+}$ and/or High N Co-Cultivation Medium in Gene Introduction Materials and Methods Immature embryos treated similarly to Example 1 were placed on the co-cultivation medium containing a one-time amount of LS Inorganic Salts or co-cultivation mediums comprising $Ca^{2+}$ at a concentration of 1.2-9.6 mM, and other LS Inorganic Salts at a one fifth concentration, or a co-cultivation medium of LS Inorganic Salts at a one fifth concentration comprising the above $Ca^{2+}$ as well as $NH_4^+$ and $NO_3^-$ at a total concentration of 62.0 mM, and the transient expression of GUS genes was thus evaluated. The medium comprising $Ca^{2+}$ at a concentration of 1.2-9.6 mM was adjusted by adding $CaSO_4$. Six to seven immature embryos were used for each experimental plot, and the test was performed twice.

Results

The average score of GUS transient expression was significantly higher when the $Ca^{2+}$ concentration was 5.2 mM-9.6 mM in the experimental plot mediums with a high nitrogen condition than in the control medium (Experimental Plots 24 to 26). It was thus confirmed that the introduction efficiency of an exogenous gene to a Sorghum immature embryo was enhanced by a high $Ca^{2+}$ high N co-cultivation medium.

TABLE 6

| Co-cultivation Medium | | Control Plot | Experimental Plot 23 | Experimental Plot 24 | Experimental Plot 25 | Experimental Plot 26 |
|---|---|---|---|---|---|---|
| $Ca^+$ Concentration (mM) | | 3.0 <br> 1 × LS | 3.6 | 5.2 | 6.9 | 9.6 |
| GUS transient expression average score | $Ca^+$ | 0.13 | 0.08 | 0 | 0 | 0 |
| | $Ca^+ + N$ | | 0.62 | 0.85 | 1.23 | 0.85 |

Example 6: Effect of High $Na^+$ and/or High N Co-Cultivation Medium in Gene Introduction

Materials and Methods

Immature embryos treated similarly to Example 1 were placed on the co-cultivation medium containing a one-time amount of LS Inorganic salt or co-cultivation mediums comprising $Na^+$ at a concentration of 0.6-250.0 mM, and LS Inorganic Salts at a one fifth concentration, or a co-cultivation medium of LS Inorganic Salts at a one fifth concentration comprising the above $Na^+$ as well as $NH_4^+$ and $NO_3^-$ at a total concentration of 62.0 mM, and the transient expression of GUS genes was thus evaluated. The medium comprising $Na^+$ at a concentration of 0.6-250.0 mM was adjusted and prepared by adding $Na_2SO_4$. Six to seven immature embryos were used for each experimental plot, and the test was performed twice.

Results

The average score of GUS transient expression was higher when the $Na^+$ concentration was 0.6 mM-150.1 mM in the experimental plot co-cultivation mediums with a high nitrogen condition than in the control medium (Experimental Plots 27 to 32). It was thus confirmed that the introduction efficiency of an exogenous gene to a *Sorghum* immature embryo was enhanced by a high $Na^+$ co-cultivation medium and a high $Na^+$ high N co-cultivation medium.

centrifugation treatment in addition to the thermal treatment reported in Gurel et al. (2009: Non-Patent Document 7), in the treatment method of immature embryos before they are infected with *Agrobacterium*.

After adding an inoculation source to immature embryos that had been pretreated (centrifugation treatment at 7,500 rpm (5,000×g) for 1 min. and a thermal treatment at 43° C. for 3 min.), similarly to Example 1 (although the *Agrobacterium* suspension medium had pH 5.8), the immature embryos were placed on a modified PHI-T medium (control plot co-cultivation medium) which is a medium based on the aforementioned co-cultivation medium, PHI-T medium (Wu et al. (2014: Non-Patent Document 12)) but having an altered constitution (LS Inorganic salt, 0.5 mg/L nicotinic acid, 0.5 mg/L pyridoxine hydrochloride salt, 1 mg/L thiamine hydrochloride salt, 100 mg/L myo-inositol, 20 g/L sucrose, 10 g/L glucose, 500 mg/L MES, 700 mg/L L-proline, 1.5 mg/L 2,4-D, 100 μM acetosyringone, 5 μM $CuSO_4 \cdot 5H_2O$, 4.0 g/L agarose, pH 5.8), or a co-cultivation medium (experimental plot) in which the $Mg^{2+}$ concentration of the modified PHI-T medium is set to 5.0 mM. The same conditions were applied to the control and the experimental plots in the culturing step following co-cultivation. Specifically, immature embryos co-cultivated at 25° C. in the dark for 4 days were placed in a modified DBC3 medium which is a medium based on the DBC3 medium (Wu et al.

TABLE 7

| Co-cultivation Medium | | Control Plot | Experimental Plot 27 | Experimental Plot 28 | Experimental Plot 29 | Experimental Plot 30 | Experimental Plot 31 | Experimental Plot 32 | Experimental Plot 33 |
|---|---|---|---|---|---|---|---|---|---|
| $Na^+$ Concentration (mM) | | 0 <br> 1 × LS | 0.6 | 1.5 | 4.5 | 45.0 | 90.1 | 150.1 | 250.0 |
| GUS transient expression average score | $Na^+$ | 0 | 0.08 | 0 | 0 | 0.17 | 0 | 0 | 0 |
| | $Na^+ + N$ | | 0.50 | 0.50 | 0.50 | 0.50 | 0.67 | 0.50 | 0 |

Example 7: Effect of High $Mg^{2+}$ Co-Cultivation Medium in Transformation

Materials and Methods

The mediums of Zhao et al. (2000: Non-Patent Document 5) and Wu et al. (2014: Non-Patent Document 12) were applied as a callus induction medium and a regeneration medium to evaluate the effect of the high $Mg^{2+}$ and/or high N co-cultivation medium against the formation of *Sorghum* transformants, but no transformant was obtained. Hence, these known mediums were modified to perform the *Sorghum* transformation experiments.

Transformation was performed using immature embryos that were subjected to a thermal treatment and a centrifugation treatment, since we confirmed in our experiments that transformants were more easily obtained by performing a 2014: Non-Patent Document 12) but having an altered constitution (LS Inorganic Salts, 1.0 mg/L thiamine hydrochloride salt, 0.25 g/L myo-inositol, 30 g/L maltose, 2.5 g/L, sorbitol, 1.0 g/L casein, 700 mg/L L-proline, 0.75 g/L glutamine, 1.0 mg/L 2,4-D, 5 μM $AgNO_3$, 7.6 μM $CuSO_4 \cdot 5H_2O$, 150 mg/L timentin, 3.5 g/L gellan gum, pH 5.8), and they were cultured at 25° C. in the dark. The immature embryos 2 weeks after inoculation were placed on a modified DBC3 medium (excluding glutamine) containing 5 mg/L Glufosinate ammonium salt (PPT) and subjected to a primary selection to be cultured at 25° C. in the dark for 1 week. Then, the immature embryos were placed on a modified DBC3 medium containing 10 mg/L PPT (excluding glutamine, and altering the sorbitol amount to 5.0 g/L), and they were subjected to a secondary selection culture at 25° C. in the dark for 2 weeks. Next, the proliferated callus was placed in a modified DBC3 medium containing 15 mg/L PPT (excluding glutamine, adding 0.5 mg/L BAP, and further altering the amount of sorbitol to 5.0 g/L), and they were subjected to tertiary selection culture at 25° C. in the dark for 1 week.

The obtained PPT resistant callus was placed on a regeneration medium (LS Inorganic Salts, 0.5 mg/L nicotinic acid, 0.5 mg/L pyridoxine hydrochloride salt, 0.1 mg/L thiamine hydrochloride salt, 100 mg/L myo-inositol, 20 g/L sucrose, 500 mg/L MES, 700 mg/L L-proline, 10 g/L ascorbic acid, 0.5 mg/L zeatin, 1 mg/L indole-3-acetic acid, 5 µM AgNO$_3$, 5 µM CuSO$_4$.5H$_2$O, 0.1 mg/L thidiazuron, 3.5 g/L gellan gum, pH 5.8), and cultured at 25° C., 35 µmol$^{-2}$s$^{-1}$ in light for 1 month. A regenerated seedling was transplanted to a modified NAB1C1 medium (LS Inorganic salt, 0.5 mg/L nicotinic acid, 0.5 mg/L pyridoxine hydrochloride salt, 0.1 mg/L thiamine hydrochloride salt, 100 mg/L myo-inositol, 20 g/L sucrose, 500 mg/L MES, 700 mg/L L-proline, 10 g/L ascorbic acid, 1 mg/L 1-naphthaleneacetic acid, 1 mg/L indole-3-acetic acid, 1 mg/L indole-3-butyric acid, 3.5 g/L gellan gum, pH 5.8) which is a medium based on NAB1C1 medium (Guoquan et al. (2013: Non-Patent Document 13)) but having an altered constitution, and further cultured at 25° C., 35 µmol$^{-2}$s$^{-1}$ in light for 1 month.

A genome DNA extracted from an individual leaf that was regenerated from a PPT resistant callus was used to confirm the existence of an introduced gene by PCR. The genome DNA was extracted from an individual leaf by using E.Z.N.A.SP Plant DNA Kit (Omega Biotek, Doraville, USA). PCR was performed by using genome DNA as a template and a primer set (atggacccagaacgacgcccggccga-catc: SEQ ID NO: 1, tcagatctcggtgacgggcaggaccggacg: SEQ ID NO: 2) for amplifying Bar gene. About 10 ng of a genome DNA as a template, 0.2 µl of Tks Gflex DNA Polymerase (Takara), 5 µl of 2×Gflex PCR Buffer (Takara), 0.5 µM each of a forward primer (SEQ ID NO: 1) and a reverse primer (SEQ ID NO: 2) for amplifying the Bar genes were added to a 10 µl PCR reaction solution, and a PCR reaction was performed by a program of once at 94° C. for 1 min., and 35 cycles at 98° C. for 10 sec. and 68° C. for 30 sec.

The existence of introduced genes was judged by determining an individual in which a band of about 500 bp was amplified by PCR as having introduced genes, and an individual for which the band did not amplify as having no introduced genes.

Results

Immature embryos that had been subjected to co-cultivation using the co-cultivation medium with high Mg$^{2+}$ of Experimental Plot 34 provided transformants with 17.6% efficiency, but no transformant was obtained when the control co-cultivation medium was used. This showed that the effect of the high Mg$^{2+}$ co-cultivation medium that was recognized in Example 2 of enhancing the introduction efficiency of Sorghum immature embryos to exogenous genes also contributed to the subsequent transformant creation efficiency.

TABLE 8

| Co-cultivation Medium | Mg$^{2+}$ concentration of co-cultivation medium | Number of immature embyros (a) | Regenerated individuals | Individuals with GUS•Bar (b) | Transformation Rate (b/a: %) |
|---|---|---|---|---|---|
| Control (Conventional Concentration) | 1.5 mM | 17 | 0 | 0 | 0.0 |
| Experimental Plot 34 (High Concentration) | 5.0 mM | 17 | 3 | 3 | 17.6 |

Example 8: Effect of High N Co-Cultivation Medium in Transformation

Materials and Methods

Immature embryos inoculated with Agrobacterium by performing a thermal treatment and a centrifugation treatment similar to Example 7 were placed on a modified PHI-T medium which is the control co-cultivation medium of Example 7, or a experimental plot co-cultivation medium which is the modified PHI-T medium with the total concentration of NH$_4^+$ and NO$_3^-$ being 85 mM or 123 mM, and the other LS Inorganic Salts having a one half concentration to perform co-cultivation. The subsequent method of selecting PPT resistant callus, a method of reproducing individuals, a PCR analysis method for evaluating whether genes were introduced to transformants were performed similarly to Example 7.

Results

Immature embryos that were subjected to co-cultivation using the co-cultivation medium of a high N experimental plot (Experimental Plots 35 and 36) in which the total concentration of NH$_4^+$ and NO$_3^-$ was 85 mM or 123 mM each provided transformants at an efficiency of 8%, but the efficiency was 4% when using a control co-cultivation medium. This showed that the effect of the high N co-cultivation medium that was recognized in Example 1 of enhancing the introduction efficiency of exogenous genes to Sorghum immature embryos also contributed to the subsequent transformant creation efficiency.

TABLE 9

| Co-cultivation Medium | N concentration of co-cultivation medium | Number of immature embyros (a) | Regenerated individuals | Individuals with GUS•Bar (b) | Transformation Rate (b/a: %) |
|---|---|---|---|---|---|
| Control (conventional concentration) | 60 mM | 25 | 1 | 1 | 4.0 |
| Experimental plot 35 (high concentration) | 85 mM | 25 | 2 | 2 | 8.0 |
| Experimental plot 36 (high concentration) | 123 mM | 25 | 2 | 2 | 8.0 |

Example 9: Effect of High $Mg^{2+}$ and High N Co-Cultivation Medium in Transformation Materials and Methods Immature embryos inoculated with *Agrobacterium* by performing a thermal treatment and a centrifugation treatment similar to Example 7 were placed on a PHI-T medium which is the control co-cultivation medium of Example 7, or a experimental plot co-cultivation medium which is the modified PHI-T medium with one half amount of LS Inorganic Salts, and $Mg^{2+}$ at a concentration of 5.0 mM, and $NH_4^+$ and $NO_3^-$ at a total concentration of 85 mM to perform co-cultivation. The subsequent method of selecting PPT resistant callus, a method of reproducing individuals, a PCR analysis method for evaluating whether genes were introduced to transformants were performed similarly to Example 7.

Results

Immature embryos that were subjected to co-cultivation using the experimental plot co-cultivation medium with a high $Mg^{2+}$ and a high N provided transformants at an efficiency of 15%, but the efficiency was 5% when using a control co-cultivation medium containing a one-time amount of LS Inorganic Salts. This showed that the effect of the high $Mg^{2+}$ and high N co-cultivation medium of enhancing the introduction efficiency of exogenous genes to *Sorghum* immature embryos that was observed in Example 3 also contributed to the subsequent transformant creation efficiency.

TABLE 10

| Co-cultivation Medium | $Mg^{2+}$ concentration of co-cultivation medium | N concentration of co-cultivation medium | Number of immature embyros (a) | Regenerated individuals | Individuals with GUS · Bar (b) | Transformation Rate (b/a: %) |
|---|---|---|---|---|---|---|
| Control (conventional concentration) | 1.5 mM | 60 mM | 20 | 1 | 1 | 5.0 |
| Experimental plot 37 (high concentration) | 5.0 mM | 85 mM | 20 | 3 | 3 | 15.0 |

A test was also performed for immature embryos which were not subjected to a centrifugation treatment and a thermal treatment before inoculation. The effect of a high $Mg^{2+}$ and/or high N co-cultivation medium against transformation was confirmed for such cases as well (data is not shown).

SEQUENCE LISTING FREE TEXT

SEQ ID NO: 1 Forward Primer
SEQ ID NO: 2 Reverse Primer

The invention claimed is:

1. A method of gene introduction into a tissue of a plant material of a genus *Sorghum* plant, comprising:
 (i) a step of preparing an immature embryo of the genus *Sorghum*;
 (ii) a step of inoculating a tissue of the immature embryo with *Agrobacterium*; and
 (iii) a co-cultivation step of culturing the tissue inoculated with the *Agrobacterium* in a presence of the *Agrobacterium*,
 wherein a medium with an increased concentration of a nitrogen source is used in at least step (iii), and a total concentration of $NH_4^+$ and $NO_3^-$ in the medium is higher than 60 mM and at most 270 mM.

2. A method of gene introduction into a tissue of a plant material of a genus *Sorghum* plant, comprising:
 (i) a step of preparing an immature embryo of the genus *Sorghum*;
 (ii) a step of inoculating a tissue of the immature embryo with *Agrobacterium*; and
 (iii) a co-cultivation step of culturing the tissue inoculated with the *Agrobacterium* in a presence of the *Agrobacterium*,
 wherein a medium with an increased concentration of a nitrogen source and magnesium ion is used at least step (iii), and a total concentration of $NH_4^+$ and $NO_3^-$ in the medium is at least 60 mM and at most 270 mM, and the magnesium ion concentration in the medium is at least 2.6 mM and at most 100 mM.

3. A method of gene introduction into a tissue of a plant material of a genus *Sorghum* plant, comprising:
 (i) a step of preparing an immature embryo of the genus *Sorghum*;
 (ii) a step of inoculating a tissue of the immature embryo with *Agrobacterium*; and
 (iii) a co-cultivation step of culturing the tissue inoculated with the *Agrobacterium* in a presence of the *Agrobacterium*,
 wherein a medium with an increased concentration of a nitrogen source and potassium ion is used in at least step (iii), and a total concentration of $NH_4^+$ and $NO_3^-$ in the medium is at least 60 mM and at most 270 mM, and the potassium ion concentration in the medium is at least 24 mM and at most 65 mM.

4. A method of gene introduction into a tissue of a plant material of a genus *Sorghum* plant, comprising:
 (i) a step of preparing an immature embryo of the genus *Sorghum*;
 (ii) a step of inoculating a tissue of the immature embryo with *Agrobacterium*; and
 (iii) a co-cultivation step of culturing the tissue inoculated with the *Agrobacterium* in the presence of the *Agrobacterium*,
 wherein a medium with an increased concentration of a nitrogen source and calcium ion is used in at least step (iii), and a total concentration of $NH_4^+$ and $NO_3^-$ in the medium is at least 60 mM and at most 270 mM, and the calcium ion concentration in the medium is at least 5.2 mM and at most 10 mM.

5. A method of gene introduction into a tissue of a plant material of a genus *Sorghum* plant, comprising:
 (i) a step of preparing an immature embryo of the genus *Sorghum*;
 (ii) a step of inoculating a tissue of the immature embryo with *Agrobacterium*; and
 (iii) a co-cultivation step of culturing the tissue inoculated with the *Agrobacterium* in the presence of the *Agrobacterium*,
 wherein a medium with an increased concentration of a nitrogen source and sodium ion is used in at least step (iii), and a total concentration of $NH_4^+$ and $NO_3^-$ in the medium is at least 60 mM and at most 270 mM, and the sodium ion concentration in the medium is at least 0.6 mM and at most 200 mM.

6. A method for producing a transformed genus *Sorghum* plant by performing steps (i) to (iii) according to the method of claim 1, further comprising:
 (iv) a resting step of culturing the tissue cultured in the co-cultivation step in a resting medium; and
 (v) a regeneration step of regenerating the tissue in a regeneration medium.

7. The method according to claim 1, further comprising at least one of the following treatments for transformation efficiency enhancement:
 a) a thermal treatment;
 b) a centrifugation treatment;
 c) a pressurization treatment;
 d) a treatment that uses a medium with an increased concentration of a metal salt including copper ion in step (ii) and/or (iii); and
 e) a treatment that uses a medium with an increased concentration of silver nitrate in step (ii) and/or (iii).

8. The method according to claim 6, further comprising a selection step between the resting step (iv) and the regeneration step (v).

9. The method according to claim 1, wherein the *Agrobacterium* is a bacterium selected from the group consisting of LBA4404, EHA101, EHA105, AGL0, AGL1, and C58C1.

10. The method according to claim 1, wherein the genus *Sorghum* plant is *Sorghum bicolor*.

* * * * *